United States Patent [19]
Geddens et al.

[11] Patent Number: 5,948,805
[45] Date of Patent: Sep. 7, 1999

[54] FUNGICIDAL MIXTURES

[75] Inventors: Ray M. Geddens, Newark, Del.; Marsha J. Martin, Columbus, Ohio

[73] Assignee: E. I. du Pont de Nemours and Company, Wilmington, Del.

[21] Appl. No.: 08/981,999

[22] PCT Filed: Jul. 3, 1996

[86] PCT No.: PCT/US96/11346

§ 371 Date: Jan. 9, 1997

§ 102(e) Date: Jan. 9, 1997

[87] PCT Pub. No.: WO97/02745

PCT Pub. Date: Jan. 30, 1997

Related U.S. Application Data

[60] Provisional application No. 60/001,088, Jul. 12, 1995.

[51] Int. Cl.[6] .......................... A01N 37/34; A01N 37/52; A01N 43/76
[52] U.S. Cl. ........................... 514/376; 514/508; 514/528
[58] Field of Search ................... 514/376, 528, 514/508

[56] References Cited

U.S. PATENT DOCUMENTS

| | | | |
|---|---|---|---|
| 3,954,992 | 5/1976 | Davidson | 424/287 |
| 4,507,310 | 3/1985 | Devoise-Lambert | 514/376 |
| 4,957,933 | 9/1990 | Geffken et al. | 514/376 |
| 5,552,554 | 9/1996 | Sternberg et al. | 548/226 |

FOREIGN PATENT DOCUMENTS

| | | |
|---|---|---|
| WO 90/12791 | 11/1990 | WIPO . |
| WO 91/15480 | 10/1991 | WIPO . |
| WO 94/11359 | 5/1994 | WIPO . |

OTHER PUBLICATIONS

U. S. Application No. 07/976,130 (Docket No. BA–8992) which is identified as a priority document in WO 94/11359 and U.S. Pat. 5,552,554. (Nov. 13, 1992) Martin.

*Primary Examiner*—Allen J. Robinson

[57] ABSTRACT

Advantageous combinations of an oxazolidinone and cymoxanil (or their agriculturally suitable salts) and their use to control fungus disease in plants are disclosed, the oxazolidinone having the formula

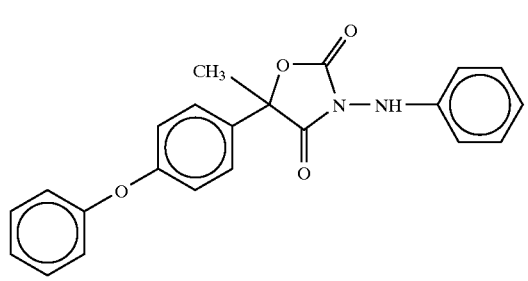

I

14 Claims, No Drawings

FUNGICIDAL MIXTURES

This application represents the national filing under 35 USC 371 of International Application No. PCT/US96/11346 filed Jul. 3, 1996 and claims priority, in part, of U.S. Application Ser. No. 60/001,088 filed Jul. 12, 1995.

BACKGROUND OF THE INVENTION

This invention pertains to agriculturally suitable compositions containing an advantageous combination of certain fungicidal oxazolidinone compounds with another fungicide, and methods for the use of such compositions to control fungus disease in certain plants.

Fungicides that effectively control plant diseases are in constant demand by growers. Plant diseases are highly destructive, difficult to control and quickly develop resistance to commercial fungicides. Combinations of pesticides are often used to facilitate disease control, to broaden spectrum of control and to retard resistance development. It is recognized in the art that the advantages of particular pesticide combinations can often vary, depending on such factors as the particular plant and plant disease to be treated, and the treatment conditions.

WO 90/12791 discloses certain oxazolidinone compounds as fungicides including 5-methyl-5-(4-phenoxyphenyl)-3-phenylamino-2,4-oxazolidinone (i.e., the Formula I compound defined herein). U.S. Pat. No. 3,954,992 discloses cymoxanil as a fungicide. Synergistic combinations of cymoxanil and oxazolidenylacetamides such as oxadixyl are disclosed in U.S. Pat. No. 4,507,310. These references neither disclose nor suggest synergistic compositions comprising an oxazolidinone and cymoxanil.

SUMMARY OF THE INVENTION

This invention pertains to an advantageous combination of cymoxanil (and/or an agriculturally suitable salt thereof) and the oxazolidinone of Formula I. This invention provides fungicidally active compositions comprising a fungicidally effective amount of a mixture of (a) at least one compound selected from the oxazolidinone of Formula I and agriculturally suitable salts thereof, and (b) at least one compound selected from cymoxanil and agriculturally suitable salts thereof, and optionally (c) at least one of a surfactant, a solid diluent or a liquid diluent wherein the weight ratio of component (a) to component (b) is from about 17:1 to about 1:100.

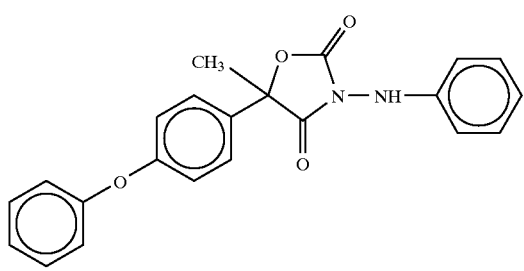

I

The compound of Formula I is also known as 5-methyl-5-(4-phenoxyphenyl)-3-phenylamino-2,4-oxazolidinone.

This invention also provides methods for controlling plant diseases caused by fungal plant pathogens comprising applying to the plant or portion thereof to be protected, or to the plant seed or seedling to be protected one of the following:

1) an effective amount of a fungicidal composition comprising (a) the compound of Formula I as defined above, or an agriculturally suitable salt thereof, (b) cymoxanil, or an agriculturally suitable salt thereof, and (c) at least one of a surfactant, a solid diluent or a liquid diluent;

2) (i) an effective amount of a first composition comprising (a) the compound of Formula I as defined above, or an agriculturally suitable salt thereof, and (c1) at least one of a surfactant, solid or liquid diluent; and (ii) an effective amount of a second composition comprising (b) cymoxanil, or an agriculturally suitable salt thereof, and (c2) at least one of a surfactant, a solid diluent or a liquid diluent, said first and second compositions applied sequentially in any order; or 3) an effective amount of a physical mixture of the first and second compositions as defined in 2 above.

The weight ratio of the compound of (a) to the compound of (b) applied is normally from about 17:1 to 1:100, and the compound of (a) and the compound of (b) are normally applied in amounts effective to provide control of the fungal disease which is greater than the additive control of that fungal disease provided by the compound of (a) and the compound of (b) individually.

DETAILED DESCRIPTION OF THE INVENTION

It has been found that combinations of the compound of Formula I and cymoxanil provide control of certain plant diseases which is substantially and surprisingly enhanced over the expected simply additive control by said components.

Cymoxanil, tradename Curzate®, is a commercially available foliar fungicide for control of late blight and downy mildew diseases, particularly for systemic and curative control of potato late blight and grape downy mildew, having the formula:

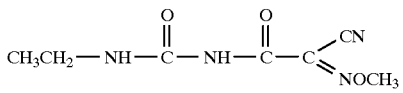

which is also known as 2-cyano-N-[(ethylamino)carbonyl]-2-(methoxyimino)acetamide.

The compound of Formula I can exist as enantiomers. One skilled in the art will appreciate that one enantiomer may be more active and/or may exhibit beneficial effects when enriched relative to the other enantiomer or when separated from the other enantiomer. Additionally, the skilled artisan knows how to separate, enrich, and/or to selectively prepare said enantiomers. Accordingly, the present invention comprises compositions of the individual enantiomers or optically active mixtures of the oxazolidinone of Formula I as well as agriculturally suitable salts thereof in admixture with cymoxanil or an agriculturally suitable salt thereof.

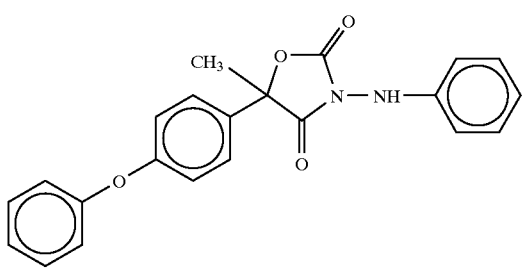

Cymoxanil can be prepared by the procedures described in U.S. Pat. No. 3,954,992. Preparation of the compositions of the present invention containing cymoxanil and the compound of Formula I is discussed later in the application.

The compound of Formula I can be prepared as depicted in Scheme 1 and described in WO 94/11359.

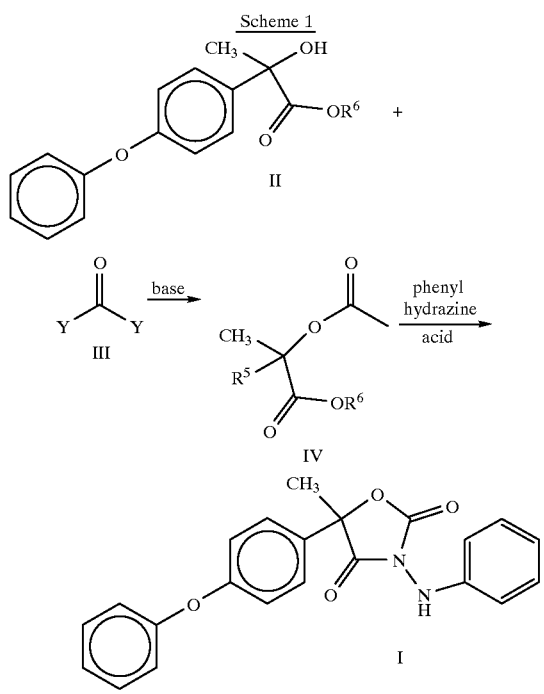

wherein:

$R^6$ is $C_1$–$C_4$ alkyl; and

Y is 1-imidazolyl or 1,2,4-triazolyl.

Reaction conditions suitable for preparing the compound of Formula I are as follows. For the conversion of esters of Formula II to compounds of Formula IV, the suitable solvents include inert organic solvents. Preferred solvents are methylene chloride, chloroform, carbon tetrachloride, hexanes, tetrahydrofuran, tert-butyl methyl ether, dioxanes, chlorobenzene, o-dichlorobenzene (ODCB), toluene, xylenes, and suitable combinations thereof. The most preferred solvents are selected from the group consisting of chlorobenzene, ODCB, toluene, and xylenes. The reaction temperatures can range from about 10° C. to about 75° C. Preferred temperatures are from about 40° C. to about 60° C. Suitable reaction pressures are from about $1.0 \times 10^5$ to about $5.1 \times 10^5$ Pascals. The preferred pressure is $1 \times 10^5$ Pascals. The reaction times are typically 1 to 24 hours, preferably 3 to 6 hours. A suitable ratio of Formula III to II is from about 1:1 to 2:1. The preferred ratio is from about 1.1:1 to 1.8:1. Suitable bases for this reaction include trialkylamines, imidazole, pyridine, picolines or other substituted pyridine derivatives.

For the conversion of compounds of Formula IV to the 2,4-oxazolidinedione of Formula I, suitable solvents are as noted above for the condensation of Formulae II and III. The preferred solvents are those disclosed above as preferred. The reaction temperatures are from about 0° C. to about 75° C. Preferred temperatures are from about 10° C. to about 50° C. Reaction pressures are from about $1.0 \times 10^5$ to about $5.1 \times 10^5$ Pascals. The preferred pressure is $1 \times 10^5$ Pascals. The reaction times are typically 1 to 24 hours, preferably 2 to 6 hours. The acids suitable for catalyzing the reaction are selected from the group consisting of alkyl and aryl carboxylic acids, trialkylammonium halides and combinations thereof. The preferred acids are acetic acid and triethylammonium chloride. The most preferred acid is triethylammonium chloride. Suitable ratios of phenylhydrazine to Formula IV is from about 2:1 to 1:1. The preferred ratio is from about 1.6:1 to 1.1:1.

The carbonylating agent of Formula III may be added as a pure compound, a solution of the pure compound in an inert solvent, or prepared in situ in the presence of the ester of Formula II. The preferred process involves preparation of the carbonylating agent in situ.

Methods for preparing compounds of Formula III, including in situ methods, from phosgene [or phosgene equivalents such as diphosgene (trichloromethyl chloroformate) or triphosgene [bis(trichloromethyl)carbonate)] and either imidazole or triazole are known in the art (see Org. Syntheses. Coll. Vol. 5, 201, (1973)). Reactions wherein HCl is liberated require a base to trap the acid. A suitable base is a trialkylamine or imidazole, or combinations thereof. The preferred base is triethylamine. 1,1'-Carbonylditriazole (Formula III wherein Y=1,2,4-triazolyl) can also be prepared by treating a metal alkali salt of triazole, preferably the potassium salt, with phosgene (or phosgene equivalent) in a solvent. Phase transfer catalysts are preferably added to reactions wherein the triazole salt has low solubility in the solvent. For example, phase transfer catalysts are preferred when xylenes or toluene is used. Any phase transfer catalyst known to one skilled in the art is suitable. Tetraalkylammonium halides are preferred. The triazole salt is prepared by treating triazole with a suitable base, such as sodium hydroxide or sodium ethoxide. The preferred relative amount of alkali metal base to triazole to phosgene is 0.5:1.0:0.6.

Base is also necessary to catalyze the condensation of Formulae II and III. As previously stated, suitable base catalysts are trialkylamines, imidazole, pyridine, picolines or other substituted pyridines. When 1,1'-carbonyldiimidazole is used (Formula III wherein Y=1-imidazolyl), the imidazole which is liberated upon reaction with Formula II serves as the catalyst. When 1,1'-carbonylditriazole is used, the preferred base is pyridine, a picoline, or a mixture of picoline isomers.

Compounds of Formula IV may be isolated and purified, or treated in situ with phenylhydrazine and acid to form the 2,4-oxazolidinedione of Formula I. The preferred method involves treatment of Formula IV in situ with phenylhydrazine. After the formation of the carbamate of Formula IV is complete, excess carbonylating agent can be decomposed by the addition of water.

The 2-hydroxycarboxylic acid esters of Formula II can be prepared by a number of methods known in the literature:

(1) They can be formed from the corresponding 2-hydroxycarboxylic acids by esterification as is well known in the literature. The 2-hydroxycarboxylic acids can be prepared from methyl ketones by formation of cyanohydrins, then hydrolysis, as is also known. For example, *Org. Syntheses*. Coll. Vol. 4, 58 (1968) teaches the preparation of atrolactic acid from acetophenone.

(2) The esters can also be synthesized from ketone cyanohydrins by treatment with alcohols in the presence of HCl to afford the iminoether hydrochlorides, followed by hydrolysis.

(3) A third method known for preparing 2-hydroxycarboxylic acids and esters involves treating 2-keto-acids or 2-keto-esters with nucleophilic-organometallic reagents such as Grignard reagents, and alkyl- and aryl-lithium reagents. For example, R. G. Salomon et al. teaches the preparation of some esters of Formula II by the addition of aryl-Grignard reagents to pyruvate esters (*J. Org. Chem.* (1982), 47, 4692). Similarly, some 2-hydroxycarboxylic acids may be prepared by the regioselective nucleophilic addition of an aryl organometallic reagent to the metal salt (e.g., sodium salt) of pyruvic acid.

(4) Another method described in the literature for preparing some 2-aryl-2-hydroxyesters and acids is by acylation of aromatic rings with activated carbonyl compounds in the presence of a protic or Lewis acid. Aromatic substrates capable of undergoing reactions of this type are benzene, diphenyl ether, and other aromatic compounds known to be of sufficient reactivity to undergo Friedel-Crafts-type reactions. In the case of mono-substituted benzene derivatives, the acylation occurs preferentially, but not necessarily exclusively, para to the point of attachment of the substituent. For example, see *Org. Syntheses*, Coll. Vol. 3, 326, (1955), Salomon et al., *J. Org. Chem.*, (1982), 47, 4692, and U.S. Pat. No. 4,922,010.

Carbonyl compounds known to undergo this reaction include pyruvate esters and acids, glyoxylate esters and acids, and diesters of oxomalonates. The acids used in the acylation reaction can either be protic in nature, for example, a mixture of acetic and sulfuric acid, or a Lewis acid such as aluminum chloride, tin tetrachloride, titanium tetrachloride, or other Lewis acid known to effect Friedel-Crafts-type reactions. The acid can be used either catalytically or in excess. In some cases, the acid may react destructively with the carbonyl substrate and excess carbonyl compound must be used.

Fungicides that effectively control plant fungi, particularly of the class Oomycetes, such as Phytophthora spp. and Plasmopara spp., are in constant demand by growers. Combinations of fungicides are often used to facilitate disease control and to retard resistance development. Mixtures of fungicides may provide significantly better disease control than could be predicted based on the activity of the individual components. This synergism has been described as "the cooperative action of two components of a mixture, such that the total effect is greater or more prolonged than the sum of the effects of the two (or more) taken independently" (see Tames, P. M. L., *Neth. J. Plant Pathology*, (1964), 70, 73–80). It has been found that compositions containing the compound of Formula I and cymoxanil exhibit synergistic effects.

The presence of a synergistic effect between two active ingredients is established with the aid of the Colby equation (see Colby, S. R. In *Calculating Synergistic and Antagonistic Responses of Herbicide Combinations*, Weeds, (1967), 15, 20–22):

$$p = A + B - \left[\frac{A \times B}{100}\right]$$

Using the methods of the Colby, the presence of a synergistic interaction between two active ingredients is established by first calculating the predicted activity, p, of the mixture based on activities of the two components applied alone. If p is lower than the experimentally established effect, synergism has occurred. In the equation above, A is the fungicidal activity in percentage control of one component applied alone at rate x. The B term is the fungicidal activity in percentage control of the second component applied at rate y. The equation estimates p, the fungicidal activity of the mixture of A at rate x with B at rate y if their effects are strictly additive and no interaction has occurred.

In this invention, fungicidal activities provided by compositions of Formula I and cymoxanil alone are compared with that of a composition of a compound of Formula I and cymoxanil. Based on the description of synergism developed by Colby, compositions of the present invention are considered to be synergistically useful. More particularly, the compositions comprising (a) at least one compound selected from 5-methyl-5-(4-phenoxyphenyl)-3-phenylamino-2,4-oxazolidinone and its agriculturally suitable salts, (b) at least one compound selected from 2-cyano-N-[(ethylamino)carbonyl]-2-(methoxyimino)acetamide and its agriculturally suitable salts, and (c) at least one of a surfactant, a solid diluent or a liquid diluent wherein the weight ratio of component (a) and component (b) is between about 17:1 and about 1:100, can be synergistic. Moreover, compositions comprising components (a) and (b) alone can be conveniently mixed with an optional diluent prior to applying to the crop to be protected. The weight ratio of component (a) to component (b) is preferably from about 8:1 to about 1:25; and is more preferably from about 4:1 to about 1:10. Of note are compositions wherein the weight ratio of component (a) to component (b) is from about 3:2 to about 1:3. Accordingly, this invention provides an improved method of combating fungi, particularly fungi of the class Oomycetes such as Phytophthora spp. and Plasmopara spp., in crops, especially potatoes, grapes and tomatoes.

The compound of Formula I and cymoxanil can be formulated in two ways:

1. the compound of Formula I and cymoxanil can be formulated separately and applied separately or applied simultaneously in an appropriate weight ratio, e.g. as a tank mix; or
2. the compound of Formula I and cymoxanil can be formulated together in the weight ratios as defined herein.

The fungicidal composition of the present invention comprises an effective amount of a mixture of the compound of Formula I and cymoxanil as defined above as the active ingredients and at least one of a surfactant, a solid diluent or a liquid diluent. The composition of this invention is typically used in formulation with an agriculturally suitable carrier comprising a liquid or solid diluent and/or a surfactant wherein the formulation is consistent with the physical properties of the active ingredients, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredients can be (micro) encapsulated and further formed into a suspension or solid formulation; alternatively the entire formulation of active ingredients can be encapsulated (or "overcoated"). Encapsulation can control or delay release of the active ingredients. Sprayable formulations can be extended in suitable media and used at spray volumes from about one to several hundred liters per hectare. High-strength compositions are primarily used as intermediates for further formulation.

The formulations will typically contain effective amounts of active ingredients, diluent and surfactant within the following approximate ranges which add up to 100 percent by weight.

|  | Weight Percent | | |
| --- | --- | --- | --- |
|  | Active Ingredients | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active materials upon preformed granular carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and U.S. Pat. No. DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are worked up in conventional ways.

EXAMPLE A

Wettable Powder

| | |
| --- | --- |
| 5-methyl-5-(4-phenoxyphenyl)-3-phenylamino-2,4-oxazolidinone | 27.9% |
| cymoxanil | 37.1% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
| --- | --- |
| 5-methyl-5-(4-phenoxyphenyl)-3-phenylamino-2,4-oxazolidinone | 5.0% |
| cymoxanil | 5.0% |
| attapulgite granules (low volatile matter, 0.71/0.30 mm; U.S.S. No. 25-50 sieves) | 90.0%. |

EXAMPLE C

Extruded Pellet

| | |
| --- | --- |
| 5-methyl-5-(4-phenoxyphenyl)-3-phenylamino-2,4-oxazolidinone | 10.7% |
| cymoxanil | 14.3% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
| --- | --- |
| 5-methyl-5-(4-phenoxyphenyl)-3-phenylamino-2,4-oxazolidinone | 10.0% |
| cymoxanil | 10.0% |

| | |
|---|---|
| blend of oil soluble sulfonates and polyoxyethylene ethers | 10.0% |
| isophorone | 70.0%. |

The compositions of this invention are useful as plant disease control agents. The present invention further comprises a method for controlling plant diseases caused by fungal plant pathogens comprising applying to the plant or portion thereof to be protected, or to the plant seed or seedling to be protected, an effective amount of a fungicidal composition of the compound of Formula I and cymoxanil. Alternatively, fungicidal compositions containing only one of a composition of the compound of Formula I or cymoxanil can be applied followed by application of the other composition. Further, separate compositions of the compound of Formula I and a composition of cymoxanil can be combined as a physical mixture prior to application, e.g., a tank mix, and applied simultaneously. In any event, the compound of Formula I and cymoxanil are desirably applied in amounts effective to provide control of a fungal disease which is greater than the additive control of that fungal disease provided by the compound of Formula I and cymoxanil individually. The compositions of this invention provide control of diseases caused by a broad spectrum of fungal plant pathogens in the Basidiomycete, Ascomycete, Deuteromycete classes and, in particular, the Oomycete class. They are effective in controlling a broad spectrum of plant diseases, particularly foliar pathogens of ornamental, vegetable, field, cereal, and fruit crops, particularly pathogens in potato, tomato and grapevines. These pathogens include *Plasmopara viticola, Phytophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerotheca fuliginea, Fusarium oxysporum, Verticillium dahliae, Pythium aphanidermatum, Phytophthora megasperma, Scierotinia sclerotiorum, Sclerotium rolfsii, Erysiphe polygoni, Pyrenophora teres, Gaeumannomyces graminis, Rynchosporium secalis, Fusarium roseum, Bremia lactucae* and other generea and species closely related to these pathogens. Of note is their use to control *Phytophthora infestans* which is a pathogen involved in various fungal diseases (for example, potato late blight and tomato late blight). Also of note is their use to control *Plasmopara viticola* which is a pathogen involved in such fungal diseases as grape downy mildew.

The compositions of this invention can also be mixed with one or more other insecticides, fungicides, nematocides, bactericides, acaricides, semiochemicals, repellents, attractants, pheromones, feeding stimulants or other biologically active compounds to form a multi-component pesticide giving an even broader spectrum of agricultural protection. Examples of such agricultural protectants with which compositions of this invention can be formulated are: insecticides such as abamectin, acephate, azinphos-methyl, bifenthrin, buprofezin, carbofuran, chlorpyrifos, chlorpyrifos-methyl, cyfluthrin, beta-cyfluthrin, deltamethrin, diafenthiuron, diazinon, diflubenzuron, dimethoate, esfenvalerate, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin (ICIA5504), benomyl, blasticidin-S, Bordeaux mixture (tribasic copper sulfate), bromuconazole, captafol, captan, carbendazim, chloroneb, chlorothalonil, copper oxychloride, copper salts, cyproconazole, cyprodinil (CGA 219417), diclomezine, dicloran, difenoconazole, dimethomorph, diniconazole, diniconazole-M, dodine, edifenphos, epoxyconazole (BAS 480F), fenarimol, fenbuconazole, fenpiclonil, fenpropidin, fenpropimorph, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl (BAS 490F), mancozeb, maneb, mepronil, metalaxyl, metconazole, myclobutanil, neo-asozin (ferric methanearsonate), oxadixyl, penconazole, pencycuron, probenazole, prochloraz, propiconazole, pyrifenox, pyroquilon, sulfur, tebuconazole, tetraconazole, thiabendazole, thiophanate-methyl, thiram, triadimefon, triadimenol, tricyclazole, triticonazole, uniconazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

Preferred for better control of plant diseases caused by fungal plant pathogens (e.g., lower use rate or broader spectrum of plant pathogens controlled) or resistance management are mixtures of a the compositions of this invention with a fungicide selected from the group azoxystrobin (ICIA5504), copper salts (including Bordeaux mixture and copper oxychloride), fosetyl-aluminum, kresoxim-methyl (BAS 490F), metalaxyl, oxadixyl and mancozeb with fosetyl-aluminum and copper salts being the most useful. Specifically preferred mixtures of the two fungicides of this invention (Compound I refers to the compound of Formula I) with an additional fungicide are selected from the group: azoxystrobin (ICIA5504) and the mixture of cymoxanil and Compound I; copper salts and the mixture of cymoxanil and Compound I; fosetyl-aluminum and the mixture of cymoxanil and Compound I; kresoxim-methyl (BAS 490F) and the mixture of cymoxanil and Compound I; metalaxyl and the mixture of cymoxanil and Compound I; oxadixyl and the mixture of cymoxanil and Compound I; and mancozeb and the mixture of cymoxanil and Compound I.

Plant disease control is ordinarily accomplished by applying an effective amount of a composition of this invention either pre- or post-infection, to the portion of the plant to be protected such as the roots, stems, foliage, fruit, seeds, tubers or bulbs, or to the media (soil or sand) in which the plants to be protected are growing. The composition can also be applied to the seed to protect the seed and seedling.

Rates of application for the compositions can be influenced by many factors of the environment and should be determined under actual use conditions. Foliage can normally be protected when treated at a rate of from less than 1 g/ha to 5,000 g/ha of aggregate active ingredient. Aggregate active ingredient is defined as the total combined weight of active ingredients. Seed and seedlings can normally be protected when seed is treated at a rate of from 0.1 to 10 g of aggregate active ingredient per kilogram of seed. Preferred foliar application of a composition of this invention are compositions containing 1 to 400 g/ha of the compound of Formula I and 4 to 240 g/ha of cymoxanil as active ingredients.

The following Examples demonstrate the compositions and methods of the present invention and provide experimental evidence for synergy between the compound of Formula I and cymoxanil in controlling late blight of potatoes and tomatoes caused by *Phytophthora infestans* and downy mildew of grapes caused by *Plasmopara viticola*. The pathogen control protection afforded by these compositions is not limited, however, to these species. However, the synergy demonstrated in the following examples was not as consistently observed under all conditions (e.g., heavy rain or washoff) or for all plant diseases.

EXAMPLE 1

Preparation of 5-Methyl-5-(4-phenoxyphenyl)-3-phenylamino-2,4-oxazolidinedione (Compound I)

A mixture of 14.3 g of ethyl 2-(4-phenoxyphenyl)lactate (34 g of a mixture containing 14.3 g of ethyl 2-(4-phenoxyphenyl)lactate and 19.7 g of diphenyl ether), 9.7 g of 1,1'-carbonyldiimidazole and 100 mL of methylene chloride was agitated at 25° C. for 19 h. Water (0.30 mL) was added and the mixture was agitated for 15 min. Then, 5 mL of acetic acid and 7.4 g of phenylhydrazine were added. After agitating at 25° C. for 24 h, 100 mL of water was added. The pH was lowered to 2 with hydrochloric acid, and the aqueous layer was removed. After washing the methylene chloride layer with 50 mL of water, the solvent was evaporated under vacuum. The oily residue was mixed with 150 mL hexane and 15 mL of ethyl acetate, heated to 65° C., cooled to 20° C., and then filtered. The solids were washed with 100 mL of a mixture of 20 mL ethyl acetate and 80 mL of hexane and then dried. The title product (15.2 g) was obtained with a m.p. of 137–139° C.

EXAMPLE 2

Synergistic Combination of 5-methyl-5-(4-phenoxyphenyl)-3-phenylamino-2,4-oxazolidinedione (Compound I) and Cymoxanil Test compositions are prepared as follows: To 182.5 mg of a 20% microemulsion containing Compound I (36.5 mg of active ingredient) is added 32 mL of distilled water to form a stock solution of Compound I. A 20% microemulsion of Compound I is prepared by mixing together 20% of Compound I, 40% N-methylpyrrolidinone and 40% Microstep H303 (all percentages by weight). Microstep H303 is an emulsifier blend available from the Stepan Co., Northfield, Ill. 60093. Cymoxanil is used as the commercially available 50% wettable powder (WP) formulation of Curzate®. A stock solution is made by adding 32 mL of distilled water to 73 mg of the wettable powder formulation (36.5 mg of active ingredient). The stock solutions are then diluted with distilled water and applied by spraying. The following dilutions are prepared to effect the application rates:

| Rate (g ai/ha)[1] | Stock Solution (mL) | Distilled water (mL) |
|---|---|---|
| 8 | 0.5 | 59.5 |
| 35 | 2 | 58 |
| 70 | 4 | 56 |
| 140 | 8 | 52 |
| 280 | 16 | 44 |

[1]grams of active ingredient per hectare.

For applications of a single active ingredient, the total volume of spray is equal to the volume of stock solution plus the volume of distilled water added to achieve the desired rate. For simultaneous application of Compound I and cymoxanil, the appropriately diluted stock solutions containing Compound I or cymoxanil are combined and then applied by spraying.

Potatoes (*Solanum tuberosum* 'Superior') grown from tissue culture are transplanted to 4-inch (10.16 cm) pots and maintained in the greenhouse. Five to six weeks after transplanting, uniform plants 6–8 inches (15.24–20.32 cm) tall are selected. The plants are sprayed with cymoxanil alone at rates of 8, 35 and 140 g ai/ha, or with Compound I alone at rates of 8, 35 and 140 g ai/ha or with combinations of cymoxanil and Compound I in all rate combinations. After spraying, the plants are maintained in a greenhouse for 6 days. Plants are then inoculated with an aerosol suspension of *P. infestans* zoospores ($2 \times 10^4$ zoospores/mL) in deionized water. The plants are then immediately placed in a humidification chamber (>98% relative humidity) for 24 hours to provide environmental conditions necessary for infection afterwards and, following a 24 hour transition period in a lighted growth chamber, the plants are returned to the greenhouse. Disease is evaluated 6 days after inoculation by recording the percentage of leaf surface with typical *P. infestans* lesions on the basal four fully expanded true leaves. Each treatment is replicated 3 times for each test. The mean percentage disease control is summarized in Table 1. Tests where the control level is greater than simply additive are indicated by an asterisk.

TABLE 1

Synergistic Effect of Compound I/Cymoxanil Combination on Potato Late Blight

| | | Percentage disease control | | | | | |
|---|---|---|---|---|---|---|---|
| | | Experimental[2] | | | Expected[3] | | |
| Compound | Rate g ai/ha[1] | Test 1 | Test 2 | Ave | Test 1 | Test 2 | Ave |
| cymoxanil | 8 | 0 | 20 | 10 | — | — | — |
| cymoxanil | 35 | 0 | 25 | 12.5 | — | — | — |

TABLE 1-continued

Synergistic Effect of Compound I/Cymoxanil Combination on Potato Late Blight

|  |  | Percentage disease control | | | | | |
|---|---|---|---|---|---|---|---|
|  |  | Experimental[2] | | | Expected[3] | | |
| Compound | Rate g ai/ha[1] | Test 1 | Test 2 | Ave | Test 1 | Test 2 | Ave |
| cymoxanil | 140 | 41 | 51 | 46 | — | — | — |
| Compound I | 8 | 69 | 77 | 73 | — | — | — |
| Compound I | 35 | 87 | 98 | 92.5 | — | — | — |
| Compound I | 140 | 90 | 98 | 94 | — | — | — |
| cymoxanil + I | 8 + 8 | *77 | *95 | *86 | 69 | 82 | 76 |
| cymoxanil + I | 8 + 35 | *98 | 98 | *98 | 87 | 98 | 93 |
| cymoxanil + I | 8 + 140 | *95 | *99 | *97 | 90 | 98 | 95 |
| cymoxanil + I | 35 + 8 | *75 | 74 | 74.5 | 69 | 83 | 76 |
| cymoxanil + I | 35 + 35 | *91 | 98 | *94.5 | 87 | 99 | 93 |
| cymoxanil + I | 35 + 140 | *98 | *100 | *99 | 90 | 99 | 95 |
| cymoxanil + I | 140 + 8 | *95 | 86 | *90.5 | 82 | 89 | 85 |
| cymoxanil + I | 140 + 35 | *98 | *100 | *99 | 92 | 99 | 96 |
| cymoxanil + I | 140 + 140 | *98 | 98 | *98 | 94 | 99 | 97 |

[1]grams of active ingredient per hectare.
[2]actual control observed.
[3]expected control calculated from Colby equation.

EXAMPLE 3

Synergistic Combination of 5-methyl-5-(4-phenoxyphenyl)-3-phenylamino-2,4-oxazolidinedione (Compound I) and Cymoxanil Test compositions are prepared as follows: A stock solution of Compound I is prepared from 1825 mg of a 2% emulsifiable concentrate (EC) containing Compound I (36.5 mg of active ingredient) as described in Example 2. A 2% EC of Compound I is prepared by dissolving 25.51 g of Compound I into a solvent mixture consisting of 37.5 g of Atlox® 3453, 37.5 g of Atlox® 3404, 62.5 g of n-butanol, and 1112.5 g of acetophenone. Atlox® 3453 and Atlox® 3494 are available from ICI Americas, Inc., New Murphy Road and Concord Pike, Wilmington, Del. 19807. A stock solution of cymoxanil is prepared from a 50% WP formulation of Curzate® in a manner similar to that described in Example 2. The stock solutions are then diluted with distilled water as described in Example 2 to effect application rates of 70g ai/ha, 140g ai/ha, and 280 g ai/ha. These dilutions are then applied to the test plants by spraying following the procedures described in Example 2.

The composition prepared above is tested as follows. The test conditions are identical as those described for Example 2 except that (i) the test rates for cymoxanil were 70 and 140 g ai/ha (ii) the test rates for Compound I were 140 and 280 g ai/ha and (iii) the plants are maintained in a greenhouse for 2 days after spraying and are then inoculated. The mean percentage disease control is summarized in Table 2. Tests where the control level is greater than simply additive are indicated by an asterisk.

TABLE 2

Synergistic Effect of Compound I/Cymoxanil Combination on Potato Late Blight

|  |  | Percentage disease control | |
|---|---|---|---|
| Compound | Rate g ai/ha[1] | Experimental[2] | Expected[3] |
| cymoxanil | 70 | 14 | — |
| cymoxanil | 140 | 56 | — |
| Compound I | 140 | 62 | — |
| Compound I | 280 | 71 | — |
| cymoxanil + I | 70 + 140 | *81 | 67 |
| cymoxanil + I | 70 + 280 | *89 | 83 |
| cymoxanil + I | 140 + 140 | *77 | 75 |
| cymoxanil + I | 140 + 280 | *91 | 87 |

[1]grams of active ingredient per hectare.
[2]actual control observed.
[3]expected control calculated from Colby equation.

EXAMPLE 4

Synergistic Combination of 5-methyl-5-(4-phenoxyphenyl)-3-phenylamino-2,4-oxazolidinedione (Compound I) and Cymoxanil A 2% EC of Compound I is prepared by the procedure described in Example 3. Stock solutions and dilutions of Compound I and Cymoxanil are prepared by the procedures described in Example 3. These dilutions are then applied to the test plants by spraying following the procedures described in Example 2.

Potatoes (*Solanum tuberosum* 'Superior') grown from tissue culture are transplanted to 4-inch (10.16 cm) pots and maintained in the greenhouse. Five to six weeks after transplanting, uniform plants 6–8 inches (15.24–20.32 cm) tall are selected. The plants are sprayed with cymoxanil alone at rates of 70 and 140 g ai/ha, or with Compound I alone at rates of 140 and 280 g ai/ha or with combinations of cymoxanil and Compound I in all rate combinations. After spraying, the plants are maintained in a greenhouse for 6 days. Plants are then inoculated with an aerosol suspension of *P. infestans* zoospores ($2 \times 10^4$ zoospores/mL) in deionized water. The plants are then immediately placed in a humidification chamber (>98% relative humidity) for 24 hours to provide environmental conditions necessary for infection afterwards. After the humidification period, plants are sprayed a second time with the same treatments applied earlier. After drying, plants are given a 24-hour transition period in a lighted growth chamber and returned to the greenhouse. Disease is evaluated 6 days after inoculation by recording the percentage of leaf surface with typical *P. infestans* lesions on the basal four fully expanded true leaves. Each treatment is replicated 3 times. The mean percentage disease control is summarized in Table 3. Tests where the control level is greater than simply additive are indicated by an asterisk.

TABLE 3

Synergistic Effect of Compound I/Cymoxanil Combination on Potato Late Blight

| | | Percentage disease control | |
|---|---|---|---|
| Compound | Rate g ai/ha[1] | Experimental[2] | Expected[3] |
| cymoxanil | 70 | 65 | — |
| cymoxanil | 140 | 91 | — |
| Compound I | 140 | 62 | — |
| Compound I | 280 | 80 | — |
| cymoxanil + I | 70 + 140 | *92 | 86 |
| cymoxanil + I | 70 + 280 | *99 | 93 |
| cymoxanil + I | 140 + 140 | *99 | 96 |
| cymoxanil + I | 140 + 280 | *100 | 98 |

[1] grams of active ingredient per hectare.
[2] actual control observed.
[3] expected control calculated from Colby equation.

EXAMPLE 5

Synergistic Combination of 5-methyl-5-(4-phenoxyphenyl)-3-phenylamino-2,4-oxazolidinedione (Compound I) and Cymoxanil This test is performed using compositions of Compound I and cymoxanil which are prepared by dissolving each compound in acetone and then diluting each solution with water containing a non-ionic surfactant to give a final stock solution consisting of the active ingredient in 1:1 acetone::water containing 0.02% by volume of a non-ionic surfactant. The dilutions are prepared in a manner similar to those described in Example 2. These dilutions are then applied to the test plants by spraying following the procedures described in Example 2.

After spraying, the plants are returned to the greenhouse. On day 1 after spraying, plants are moved into a humidification chamber (>98% relative humidity) for 8 hours at which time they are placed in a lighted growth chamber (20° C.) for 16 hours. This cycle is repeated on day 2 after spraying. On day 3 after spraying, plants are returned to the greenhouse and maintained for 3 days until inoculation.

Plants are then inoculated with an aerosol suspension of *P. infestans* zoospores ($2 \times 10^4$ zoospores/mL) in deionized water. The plants are then immediately placed in a humidification chamber (>98% relative humidity) for 24 hours to provide environmental conditions necessary for infection afterwards and, following a 24 hour transition period in a lighted growth chamber, the plants are returned to the greenhouse. Disease is evaluated 6 days after inoculation by recording the percentage of leaf surface with typical *P. infestans* lesions on the basal four fully expanded true leaves. Each treatment is replicated 5 times for each test. The test is repeated twice and the mean percentage disease control summarized in Table 4 is the average of both tests. Treatments where the control level is greater than simply additive are indicated by an asterisk.

TABLE 4

Synergistic Effect of Compound I/Cymoxanil Combination on Potato Late Blight

| | | Percentage disease control | |
|---|---|---|---|
| Compound | Rate g ai/ha[1] | Experimental[2] | Expected[3] |
| cymoxanil | 100 | 38 | — |
| cymoxanil | 250 | 47 | — |
| cymoxanil | 625 | 41 | — |
| Compound I | 15 | 59 | — |
| Compound I | 30 | 66 | — |
| Compound I | 60 | 91 | — |
| Compound I | 120 | 94 | — |
| cymoxanil + I | 100 + 15 | 48 | 75 |
| cymoxanil + I | 100 + 30 | *80 | 79 |
| cymoxanil + I | 100 + 60 | *98 | 94 |
| cymoxanil + I | 100 + 120 | 96 | 96 |
| cymoxanil + I | 250 + 15 | 45 | 78 |
| cymoxanil + I | 250 + 30 | *84 | 82 |
| cymoxanil + I | 250 + 60 | *97 | 95 |
| cymoxanil + I | 250 + 120 | 95 | 97 |
| cymoxanil + I | 625 + 15 | 68 | 76 |
| cymoxanil + I | 625 + 30 | *96 | 80 |
| cymoxanil + I | 625 + 60 | *100 | 95 |
| cymoxanil + I | 625 + 120 | 99 | 96 |

[1] grams of active ingredient per hectare.
[2] actual control observed, average of two separate tests.
[3] expected control calculated from Colby equation.

EXAMPLE 6

Synergistic Combination of 5-methyl-5-(4-phenoxyphenyl)-3-phenylamino-2,4-oxazolidinedione (Compound I) and Cymoxanil This test is performed using compositions of Compound I and cymoxanil which are prepared by dissolving each compound in acetone and then diluting each solution with water containing a non-ionic surfactant to give a final stock solution consisting of the active ingredient in 1:1 acetone::water containing 0.02% by volume of a non-ionic surfactant. The dilutions are prepared in a manner similar to those described in Example 2. These dilutions are then applied to the test plants by spraying following the procedures described in Example 2.

Seedling grape plants (*Vitis vinifera* 'Chardonnay') are grown in 2-inch (5-cm) square plastic pots and maintained in a growth chamber at 27° C. and 16-hour photoperiod. When plants are approximately 24 inch (5–10 cm) tall, uniform plants are selected for testing. Plants are sprayed with cymoxanil alone at 7.8, 31.3, 125 and 500 g ai/ha, or with Compound I alone at rates of 0.31, 1.25, 5 and 20 g ai/ha or with combinations of cymoxanil and Compound I in all rate combinations. After spraying, plants are returned to the growth chamber. On day 1 after spraying, plants are moved into a humidification chamber (>98% relative humidity) for 16 hours at which time they are returned to the growth chamber for 8 hours. This cycle is repeated on days 2,4 and 5 after spraying. On day 6 after spraying, plants are returned to the growth chamber and maintained for 1 day until inoculation. Plants then are inoculated with an aerosol suspension of *Plasmopara viticola* zoospores ($2.5 \times 10^4$ zoospores/mL) in deionized water. Inoculated plants immediately are placed in a humidification chamber for 24 hours to provide environmental conditions necessary for infection. Plants then are returned to the growth chamber for 6 days, at which time they are returned to the humidification chamber for 24 hours to induce sporulation. Disease severity is evaluated by recording the percentage of leaf surface with typical *P. viticola* lesions and sporulation on the basal three fully expanded true leaves of each plant. Each treatment is replicated 5 times for each test. The mean percentage disease control [((% disease in check)–(% disease in treated))/(% disease in check)×100] is summarized in Table 5. Tests where the control level is greater than simply additive are indicated by an asterisk.

TABLE 5

Synergistic Effect of Compound I/Cymoxanil Combination on Grape Downy Mildew

| Compound | Rate g ai/ha[1] | Experimental[2] | Expected[3] |
|---|---|---|---|
| cymoxanil | 7.8 | 2 | — |
| cymoxanil | 31.3 | 3 | — |
| cymoxanil | 125 | 28 | — |
| cymoxanil | 500 | 99 | — |
| Compound I | 0.31 | 20 | — |
| Compound I | 1.25 | 18 | — |
| Compound I | 5 | 71 | — |
| Compound I | 20 | 99 | — |
| cymoxanil + I | 7.8 + 0.31 | 4 | 22 |
| cymoxanil + I | 7.8 + 1.25 | 15 | 20 |
| cymoxanil + I | 7.8 + 5 | *77 | 72 |
| cymoxanil + I | 7.8 + 20 | 99 | 99 |
| cymoxanil + I | 31.3 + 0.31 | 2 | 22 |
| cymoxanil + I | 31.3 + 1.25 | 16 | 20 |
| cymoxanil + I | 31.3 + 5 | 64 | 72 |
| cymoxanil + I | 31.3 + 20 | 98 | 99 |
| cymoxanil + I | 125 + 0.31 | 34 | 47 |
| cymoxanil + I | 125 + 1.25 | *87 | 41 |
| cymoxanil + I | 125 + 5 | *96 | 79 |
| cymoxanil + I | 125 + 20 | 99 | 99 |
| cymoxanil + I | 500 + 0.31 | *100 | 99 |
| cymoxanil + I | 500 + 1.25 | 100 | 100 |
| cymoxanil + I | 500 + 5 | 100 | 100 |
| cymoxanil + I | 500 + 20 | 99 | 100 |

[1] grams of active ingredient per hectare.
[2] actual control observed, average of two separate tests.
[3] expected control calculated from Colby equation.

EXAMPLE 7

Synergistic Combination of 5-methyl-5-(4-phenoxyphenyl)-3-phenylamino-2,4-oxazolidinedione (Compound I) and Cymoxanil Test compositions are prepared as follows: A portion of a 200 g/L suspension concentrate (20% SC) containing Compound I is diluted with 2000 parts of distilled water to form a 100 ppm test solution of Compound I. A 200 g/L suspension concentrate of Compound I is prepared from Compound I (204.08 g, 98%), Supermontaline SLT 70 (4.00 g), monopropylene glycol (50.00 g), Rhodorsil 454 (2.00 g), acetic acid (33.67 g, 80%), sodium acetate trihydrate (62.00 g), Bronopol (1.00 g), Attagel 50 (10.00 g), water (509.25 g), Emcol® 4100 (50.00 g), Culminal MHPC50 (1.00 g) and Atplus 469 (200.00 g) by preparation of a slurry by combining the Compound I, the Supermontaline SLT 70, the monopropylene glycol, half of the Rhodorsil 454, the acetic acid, the sodium acetate trihydrate, the Bronopol, the Attagel 50, the main part of the water, the Emcol® 4100, the Culminal MHPC50 and the Atplus 469 (as a 5% aqueous solution prepared with part of the water) under mixing; the slurry is then agitated for one hour before being wet milled with a Dynomill; the milling chamber is 85–87% filled (by volume) with glass beads having a diameter range of 0.5–0.75 mm, the peripheral speed of the mill discs is adjusted to 14 m/s, the slurry is fed to the mill at a rate of 40 mL/min and two passes are necessary to get the desired particle size (average particle size below 1 elm); the remaining half of the Rhodorsil 454, the Atplus 469 and the remaining part of the water are successively added under agitation and the suspension is agitated for a half-hour. Cymoxanil is used as the commercially available 50% wettable powder (WP) formulation of Curzate®. A portion of the 50% WP of cymoxanil is diluted with 5000 parts of distilled water to form a 100 ppm test solution of cymoxanil. A portion of a 100 g/L+100 g/L suspension concentrate (10%+10% SC) containing Compound I and cymoxanil is diluted with 1000 parts and 2000 parts of distilled water to form 100+100 ppm and 50+50 ppm test solutions of Compound I and cymoxanil, respectively. A 100 g/L +100 g/L suspension concentrate (10%+10% SC) of Compound I and cymoxanil is prepared from Compound I (102.04 g, 98%), cymoxanil (104.17 g, 96%), Supermontaline SLT 70 (2.00 g), monopropylene glycol (50.00 g), Rhodorsil 454 (2.00 g), acetic acid (26.73 g, 80%), sodium acetate trihydrate (16.37 g), Bronopol (1.00 g), Attagel 50 (2.50 g), Reax 85 (25.00 g), Morwet D425 (12.5 g), Aerosil 200 (2.50 g), Kelzan® S (0.10 g), Brij 78 (200.00 g) and water (552.66 g) by preparation of a slurry by adding the main part of Compound I and heating to 60° C.; adding the Brij 78, the acetic acid and the sodium acetate trihydrate under mixing and waiting until the Brij 78 is completely dissolved; the Supermontaline SLT 70, the monopropylene glycol, half of the Rhodorsil 454, the Bronopol, the Attagel 50, the Reax 85, the Morwet D425, Aerosil 200, the remaining part of Compound I and the cymoxanil are added under mixing while the slurry is cooling to room temperature; the slurry is then agitated for one hour before being wet milled with a Dynomill; the milling chamber is 85–87% filled (by volume) with glass beads having a diameter range of 0.5–0.75 mm, the peripheral speed of the mill discs is adjusted to 14 m/s, the slurry is fed to the mill at a rate of 40 mL/min and two passes are necessary to get the desired particle size (average particle size below 1 $\mu$m); the remaining half of the Rhodorsil 454 and the Kelzan® S (as a 2% aqueous solution prepared with the remaining part of the water) are added to the milled slurry under agitation and the suspension is agitated for a half-hour.

Tomatoes (var. Houryu) are grown in a greenhouse. The test has five replicates (each replicate of one plant per pot). Test solutions are applied at 100 mL per pot (equivalent to 3000 L/ha; 100 ppm and 50 ppm test solutions provide application rates equivalent to 300 g/ha and 150 g/ha, respectively). Plants are sprayed the following day with a suspension of zoospores of *Phytophthora infestans*, the cause of tomato late blight. This inoculation is done using a small sprayer to deposit inoculum to eight leaves on each plant. After inoculation, pots are kept in a lighted incubator at 23° C. and 100% relative humidity for two days. All eight inoculated leaves per plant are evaluated the following day by recording the percentage of leaf surface with *P. infestans* lesions. The mean percentage disease control is summarized in Table 6.

Treatments where the control level is greater than simply additive are indicated by an asterisk.

TABLE 6

Synergistic Effect of Compound I/Cymoxanil Combination on Tomato Late Blight

| Compound | Rate g ai/ha[1] | Percentage disease control | |
|---|---|---|---|
| | | Experimental[2] | Expected[3] |
| cymoxanil (50% WP) | 300 | 93 | — |
| Compound I (20% SC) | 300 | 74 | — |
| cymoxanil + I (10% + 10% SC) | 300 + 300 | *100 | 98 |
| cymoxanil + I (10% + 10% SC) | 150 + 150 | *100[4] | — |

[1] grams of active ingredient per hectare.
[2] actual control observed, average of two separate tests.
[3] expected control calculated from Colby equation.
[4] 300 total g ai/ha of the 1:1 composition provided greater control than 300 g ai/ha of either compound alone.

What is claimed is:

1. A fungicidal composition comprising: a synergistic fungicidally effective amount of a mixture of (a) at least one compound selected from 5-methyl-5-(4-phenoxyphenyl)-3-phenylamino-2,4-oxazolidinone and agriculturally suitable salts thereof, and (b) at least one compound selected from cymoxanil and agriculturally suitable salts thereof, wherein the weight ratio of component (a) to component (b) is from 17:1 to 1:100.

2. A fungicidal composition of claim 1 further comprising at least one of a surfactant, a solid diluent or a liquid diluent.

3. A fungicidal composition of claim 2 wherein the weight ratio of component (a) to component (b) is from 8:1 to 1:25.

4. A fungicidal composition of claim 3 wherein the weight ratio of component (a) to component (b) is from 4:1 to 1:10.

5. A fungicidal composition of claim 4 wherein the weight ratio of component (a) to component (b) is from 3:2 to 1:3.

6. A method for controlling plant diseases caused by fungal plant pathogens comprising: applying to the plant or portion thereof to be protected, or to the plant seed or seedling to be protected, an effective amount of a fungicidal composition comprising (a) the compound of Formula I

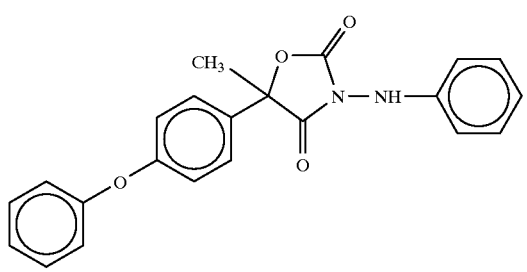

or an agriculturally suitable salt thereof, (b) cymoxanil, or an agriculturally suitable salt thereof, and (c) at least one of a surfactant, a solid diluent or a liquid diluent; the weight ratio of the compound of (a) to the compound of (b) applied being from about 17:1 to 1:100, and the compound of (a) and the compound of (b) being applied in amounts effective to provide synergistic control of the fungal disease.

7. The method of claim 6 wherein the fungal plant pathogen is *Phytophthora infestans*.

8. The method of claim 6 wherein the fungal plant pathogen is *Plasmopara viticola*.

9. A method for controlling plant diseases caused by fungal plant pathogens comprising: applying sequentially in any order to the plant or portion thereof to be protected, or to the plant seed or seedling to be protected, (i) an effective amount of a first composition comprising (a) the compound of Formula I

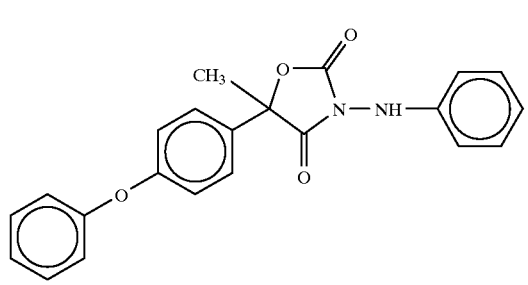

or an agriculturally suitable salt thereof, and (c1) at least one of a surfactant, a solid diluent or a liquid diluent; and (ii) an effective amount of a second composition comprising (b) cymoxanil, or an agriculturally suitable salt thereof, and (c2) at least one of a surfactant, a solid diluent or a liquid diluent; the weight ratio of the compound of (a) to the compound of (b) applied being from about 17:1 to 1:100, and the compound of (a) and the compound of (b) being applied in amounts effective to provide synergistic control of the fungal disease.

10. A method for controlling plant diseases caused by fungal plant pathogens comprising: applying to the plant or portion thereof to be protected, or to the plant seed or seedling to be protected, an effective amount of a physical mixture of (i) a first composition comprising (a) the compound of Formula I

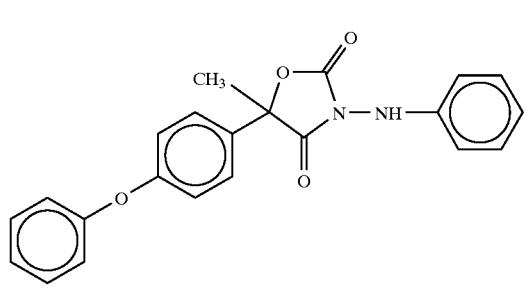

or an agriculturally suitable salt thereof, and (c1) at least one of a surfactant, a solid diluent or a liquid diluent; and (ii) a second composition comprising (b) cymoxanil or an agriculturally suitable salt thereof and (c2) at least one of a surfactant, a solid diluent or a liquid diluent; the weight ratio of the compound of (a) to the compound of (b) applied being from about 17:1 to 1:100, and the compound of (a) and the compound of (b) being applied in amounts effective to provide synergistic control of the fungal disease.

11. The method of claim 9 wherein the fungal plant pathogen is *Phytophthora infestans*.

12. The method of claim 9 wherein the fungal plant pathogen is *Plasmopara viticola*.

13. The method of claim 10 wherein the fungal plant pathogen is *Phytophthora infestans*.

14. The method of claim 10 wherein the fungal plant pathogen is *Plasmopara viticola*.

* * * * *